United States Patent [19]

Schmidtke et al.

[11] Patent Number: 5,357,960
[45] Date of Patent: Oct. 25, 1994

[54] METHOD AND APPARATUS FOR THE QUANTITATIVE DETERMINATION OF OPTICALLY ACTIVE SUBSTANCES

[75] Inventors: Gerhard Schmidtke, Freiburg; Wolfgang Riedel, Neuenburg; Helmut Wolf, Merzhausen, all of Fed. Rep. of Germany

[73] Assignee: Siemens Aktiengesellschaft, Munich, Fed. Rep. of Germany

[21] Appl. No.: 761,848
[22] PCT Filed: Oct. 6, 1989
[86] PCT No.: PCT/EP89/01175
  § 371 Date: Jan. 30, 1992
  § 102(e) Date: Jan. 30, 1992
[87] PCT Pub. No.: WO90/04163
  PCT Pub. Date: Apr. 19, 1990

[30] Foreign Application Priority Data
  Oct. 7, 1988 [DE] Fed. Rep. of Germany ....... 3834160
  Mar. 13, 1989 [DE] Fed. Rep. of Germany ....... 3908114

[51] Int. Cl.⁵ ................................................. A61B 5/00
[52] U.S. Cl. ..................................... 128/633; 356/39; 356/364
[58] Field of Search ...................... 128/633–634, 128/664–665; 356/39, 364, 366, 368; 422/82.05

[56] References Cited

U.S. PATENT DOCUMENTS

| | | |
|---|---|---|
| 3,963,019 | 6/1976 | Quandt ........................ 128/633 |
| 4,014,321 | 3/1977 | March ........................ 128/633 |
| 4,040,718 | 8/1977 | Bjorklund et al. . |
| 4,105,337 | 8/1978 | Bjorklund et al. . |
| 4,427,889 | 1/1984 | Müller ........................ 250/339 |
| 4,901,728 | 2/1990 | Hutchison ................. 128/633 |

FOREIGN PATENT DOCUMENTS

| | | |
|---|---|---|
| 0030610 | 10/1980 | European Pat. Off. . |
| 2724543 | 12/1978 | Fed. Rep. of Germany . |
| 2944113 | 12/1987 | Fed. Rep. of Germany . |

*Primary Examiner*—Angela D. Sykes
*Attorney, Agent, or Firm*—Hill, Steadman & Simpson

[57] ABSTRACT

A method and apparatus for the quantitative determination of optically active substances includes two light-emitting diodes, each with a respective collimator lens and polarization filter, a cell filled with dialysate, an analyzer, a detector and measurement and evaluation electronics. The clocked light of the light-emitting diodes is linearly polarized by the polarization filters. The polarization directions differ by a few degrees. The polarization direction of the analyzer is aligned essentially perpendicularly relative to the polarization filters, such that the radiation of the two light-emitting diodes passing through an optically non-rotating dialysate generates the same photosignal in the detector. The polarization of the radiation passing through an optically rotating dialysate, by contrast, is rotated farther in the same direction, so that the detector receives two different photosignals from the light-emitting diodes from which the concentration of optically active substances can be deduced on the basis of comparison. The cell has a chamber filled with a reference fluid, through which the radiation of the two light-emitting diodes passes. The passing through the reference fluid radiation is registered with a further photodiode and is compared for an automatic signal balancing.

14 Claims, 5 Drawing Sheets

METHOD AND APPARATUS FOR THE QUANTITATIVE DETERMINATION OF OPTICALLY ACTIVE SUBSTANCES

BACKGROUND OF THE INVENTION

1. Field of the Invention

The present invention relates to a method and an apparatus for the quantitative determination of the concentration of optically active substances, particularly glucose, in the body fluid of a patient, by polarimetry. The quantity of optically active substances is determined by a comparison signal, such as a difference or quotient signal. The present invention includes a first light source with which a first linear polarized light beam is generated that transilluminates the substance to be analyzed and charges a detector via an analyzer.

2. Description of the Invention

German Published Application 29 44 113 and EP-A 0 030 610 disclose methods and apparatus for the quantitative determination of optically active substances by polarimetry. In these methods, the specimen of the optically active substance is illuminated with linearly polarized light that has passed through a Faraday modulator. After the light has passed through the modulator, the light ray is divided into a measurement ray and a reference ray, both of which are detected separately by a detector, whereby a quotient or difference signal is formed from the signals obtained by the detector, this quotient or difference signal being utilized for the quantitative determination of an optically active substance in the transilluminated specimen.

The apparatus of this method has a complicated optical structure that is considerably expensive to miniaturize. The method of the prior art utilizes a Faraday modulator whose means for generating a magnetic field has a high power consumption, and thus, only enables short local mode operating in vivo.

SUMMARY OF THE INVENTION

It is an object of the present invention to provide a method and an apparatus for the quantitative determination of optically active substances that allow for a simple miniaturization of the apparatus, with low power consumption, such that an implantation of the apparatus in vivo is effective over a long period of time.

The above object is inventively achieved in a method including the steps of selectively generating a first linearly polarized light beam in a first fixed polarization direction with a first light source, selectively generating a second linearly polarized light beam in a second fixed polarization direction with a second light source, the second fixed polarization direction deviating by a predetermined angle from the first fixed polarization direction, alternately transilluminating a substance to be analyzed with the first and second linearly polarized light beams, by alternately switching the first and second light sources on and off with a switching frequency, to produce first and second substantially alternating beams, directing the first and second alternating beams through an analyzer to a detector to produce first and second detector signals, and generating a comparison signal with the first and a second detector signals to determine the concentration of optically active substances in the substance to be analyzed.

The above object is further achieved in an apparatus including a first light source for selectively generating a first polarized light beam, linearly polarized in a first polarization direction, a second light source for selectively generating a second polarized in a first polarization direction, a second light source for selectively generating a second polarized light beam, linearly polarized in a second polarized direction, a switching frequency for alternately actuating the first and second light source means, an analyzer for collecting the first and second light beams, after passage of the first and second light beams through a substance to be analyzed, and for imaging the first and second light beams, a detector for collecting the first and second light beams imaged by the analyzer and for generating first, and second photosignal outputs from the first and second light beams imaged by the analyzer onto the detector, and control and evaluation electronics for selectively storing the first and second photosignal outputs and for generating comparison signals using the first and second photosignal outputs, the comparison signals indicating the concentration of optically active substances to be analyzed.

The use of two differently linearly polarized light rays that can be generated in a simple and power-saving manner by two semiconductor light sources, whose light emission is controlled in chronological alternation with a switching frequency and whose fixed polarization directions deviate from one another by a predetermined angle, allows for a high resolution in the determination of the concentration of optically active substances in a transilluminated solution, given low power consumption of the electrical and electronic components.

The rigid structure of the apparatus of the present invention is devoid of mechanically moving parts, and has two fixed beam paths, thereby allowing for a high signal-to-noise ratio.

In addition, the use of a phase-sensitive documentation of the measured signals by a lock-in technique further increases the signal-to-noise ratio.

Further, the use of light-emitting or semiconductor diodes in the apparatus of the present invention allows for space-saving integrateability of selective components of the apparatus on printed circuit boards.

Four exemplary embodiments of the invention are set forth in greater detail below with reference to the following drawings.

DESCRIPTION OF THE PREFERRED EMBODIMENTS

Figure 1:
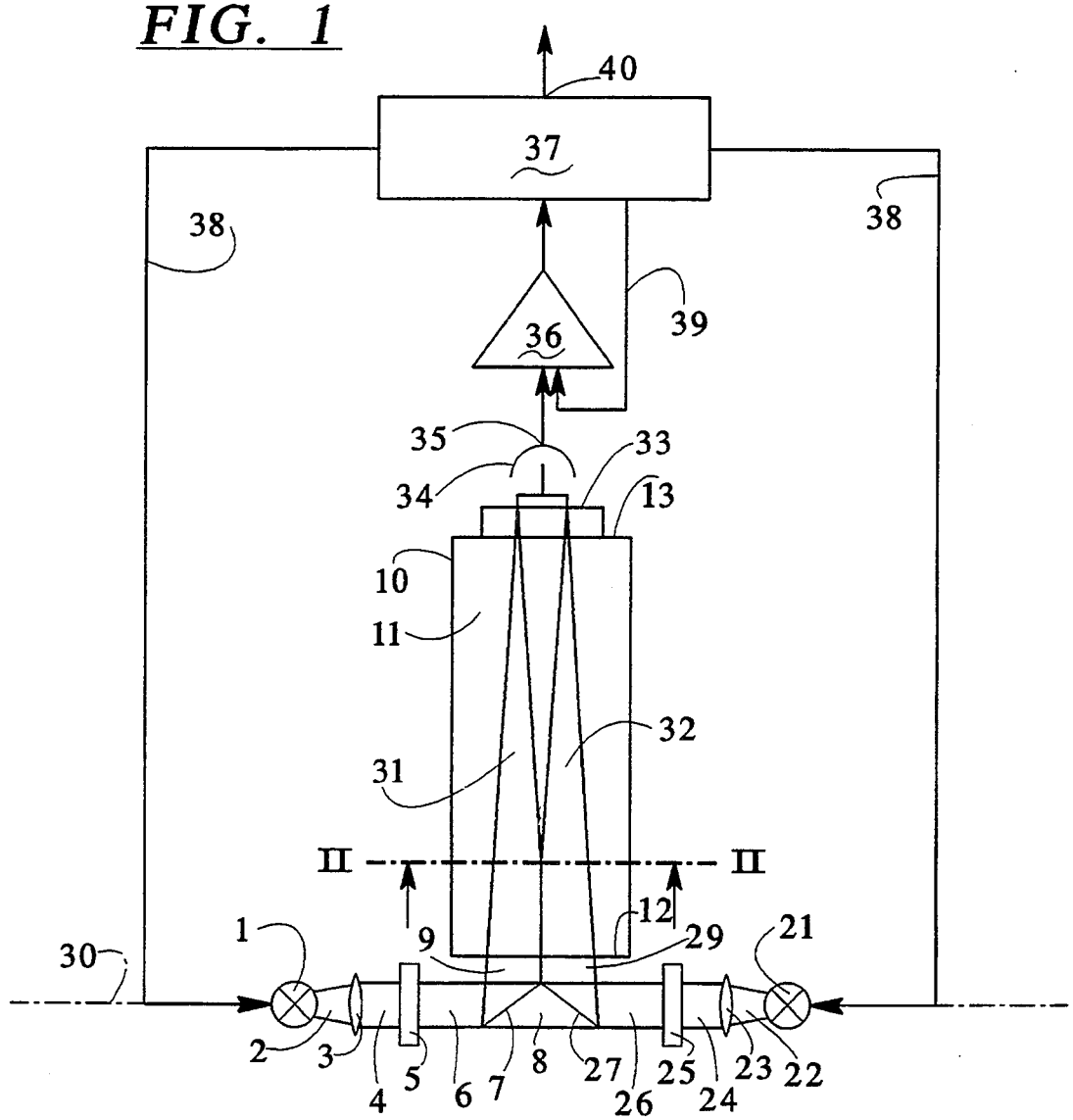
FIG. 1 is a schematic illustration of an apparatus for the quantitative determination of optically active substances conforming to a first exemplary embodiment.

FIG. 1 schematically shows an apparatus for the quantitative determination of optically active substances in vivo, conforming to a first exemplary embodiment. The apparatus includes a first light-emitting diode 1 and a second light-emitting diode 21 that emit light having essentially the same wavelength. The wavelength of the emitted light can range from 400 nanometers to 900 nanometers. It is also contemplated that the two light-emitting diodes 1, 21 could be replaced by semiconductor lasers that operate in the same wavelength range.

It is assumed for illustration in FIG. 1 that both light-emitting diodes 1, 21 are operated simultaneously. When using the apparatus of the present invention, this only occurs for adjustment or testing purposes. During a measuring operation, the two light-emitting diodes 1, 21 emit light intermittently.

The first light-emitting diode 1 generates a first divergent light beam 2. The first divergent light beam 2 is collimated into a first parallel light beam 4 by a first collimator lens 3.

The first parallel light beam 4 traverses a first polarization filter 5 that linearly polarizes the light emitted by the first light-emitting diode 1. If laser diodes are used, the laser light of the laser diode that replaces the first light-emitting diode 1 is re-polarized by the first polarization filter 5. The polarization of a first polarized light beam 6 that has passed through the first polarization filter 5 should optimally have a polarization ratio of 100:1.

The first polarized light beam 6 charges a first collimating mirror 7 that is arranged on a supporting wedge 8. The first collimating mirror 7 deflects the first polarized light beam 6 into a first convergent light beam 9.

The first convergent light beam 9 passes through a cell 10 that is filled with a dialysate 11 to be analyzed. The cell 10 is cuboid with a rectangular front wall 12 and a rectangular back wall 13. The front wall 12 of the cell 10 is transparent for the wavelength of the emitted light of the two light-emitting diodes 1, 21. The back wall 13 of the cell 10 is also transparent. The cell 10 preferably has two bores (not shown), one in the proximity of the front wall 12 and one in the proximity of the back wall 13, for the flow-through of the dialysate 11.

The second light-emitting diode 21 generates a second divergent light beam 22. The second divergent light beam 22 is collimated by a second collimator lens 23 into a second parallel light beam 24.

The second parallel light beam 24 traverses a second polarization filter 25 that linearly polarizes the light that is emitted by the second light-emitting diode 21. If laser diodes are used, the laser light of the laser diode that replaces the second light-emitting diode 21 is re-polarized by the second polarization filter 25. The polarization of a second polarized light beam 26 that has passed through the second polarization filter 25 should have a polarization ratio corresponding to that of the first polarized light beam 6.

The exact polarization direction of the second polarized light beam 26 in relation to the polarization direction of the first polarized light beam 6 shall be set forth below with reference to FIG. 2.

The second polarized light beam 26 charges a second collimating mirror 27 that is arranged on the supporting wedge 8 opposite the first collimating mirror 7. The second collimating mirror 27 deflects the second polarized light beam 26 into a second convergent light beam 29.

The second convergent light beam 29 also passes through the cell 10 that is filled with the dialysate 11 to be analyzed.

The two light-emitting diodes 1, 21 and the light beams 2, 4, 6, 22, 24 and 26 emanating from them are directed in alignment with respect to an axis 30. The beam constriction of the two polarized light beams 6, 26 is of essentially the same size. The two collimating mirrors 7, 27 have the same imaging properties.

The symmetry plane of the first collimating mirror 7 forms a substantially obtuse angle with the symmetry plane of the second collimating mirror 27. The obtuse angle is only slightly greater than a right angle, such that both the first convergent light beam 9 and the second convergent light beam 29 pass through the front wall 12 of the cell 10 and emerge from the cell 10 essentially through the same surface portion of the back wall 13, after the first convergent light beam 9 has passed through a first volume quantity 31 of the dialysate 11 and the second convergent light beam 29 has passed through a second volume quantity 32 of the dialysate 11. A first volume quantity 31 preferably has an optimally large, shared part with the second volume quantity 32 (not shown).

The two convergent light beams 9, 29 are incident on an analyzer 33 through the transparent back wall 13 of the cell 10, and are ultimately imaged onto a detector 34.

In a simplified embodiment, the mirrors 7, 27 are made planar, and the focal lengths of the collimator lenses 3, 23 are selected such that the divergent light of the light-emitting diodes 1, 21 is convergently imaged onto the detector 34, analogous to the beam guidance, or first and second volume quantity, 31, 32.

The polarization direction of the radiation that the analyzer 33 allows to pass shall be described below with reference to FIG. 2.

Based on the efficient utilization of the light sources employed, a maximum photosignal 35 is generated in the detector 34 with the imaging of the two light-emitting diodes 1, 21 onto the detector 34. The photosignal 35 charges a lock-in amplifier 36 that has its output connected to an input of a control and evaluation circuit 37. The control and evaluation circuit 37 controls the two light-emitting diodes 1, 21 by means of control lines 38, and provides a reference signal for the lock-in amplifier 36 by means of a reference control line 39. A regulating signal 40, that can be generated in the control and evaluation circuit 37, is available for the control of an insulin pump (not shown in the drawing), or for an external display.

The alignment of the various polarization directions of the two polarization filters 5, 25 and of the analyzer 33 relative to one another is discussed below with reference to the illustration of FIG. 2. The drive of the two light-emitting diodes 1, 21 and the signal processing of the photosignal 35 of 10 the detector 34 in the lock-in amplifier 36 and in the control and evaluation circuit 37 are also discussed below with reference to the illustration of FIG. 2.

Figure 2:
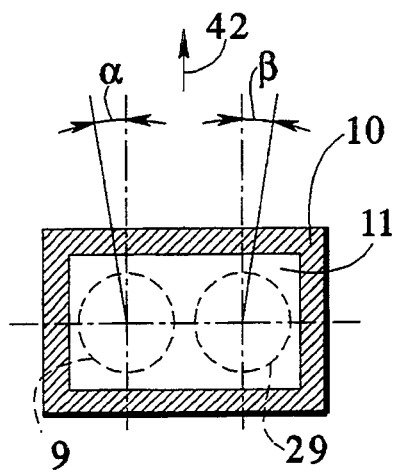
FIG. 2 is a cross-sectional view taken generally along the line II—II of FIG. 1.

FIG. 2 illustrates a cross-sectional view taken along the line II—II of FIG. 1. The cell 10 is first filled with the optically non-active dialysate 11 and is transilluminated by the two convergent light beams 9, 29 that, for illustrative purposes, are indicated by two dot-dashed circles placed a considerable distance apart. Preferably, however, the regions of the convergent light beams 9 and 29 overlap close to the front wall 12 of the cell 10.

An arrow 42 illustrates the polarization direction for light in the plane of the cross section through the cell 10. The first polarization filter 5 is arranged such that the polarization of the first convergent light beam 9 deviates, by a small, predetermined angle $\alpha$, from the polarization direction illustrated by the arrow 42. The second polarization filter 25 is arranged such that the polarization of the second convergent light beam 29 deviates, by a small, predetermined angle $\beta$, from the polarization direction illustrated by the arrow 42. In FIG. 2, the angles $\alpha$ and $\beta$ point away from the arrow 42.

In yet another embodiment of the apparatus of the present invention, the angles $\alpha$ and $\beta$ can have an identical direction, as seen proceeding from the arrow 42. The polarization directions of the first and second convergent light beams 9, 21 that deviate from the polarization direction illustrated by the arrow 42 must differ merely from one another.

The polarization direction of the analyzer 33 (not shown in the cross section of FIG. 2) is essentially perpendicular to the direction illustrated by the arrow 42.

Figure 3:
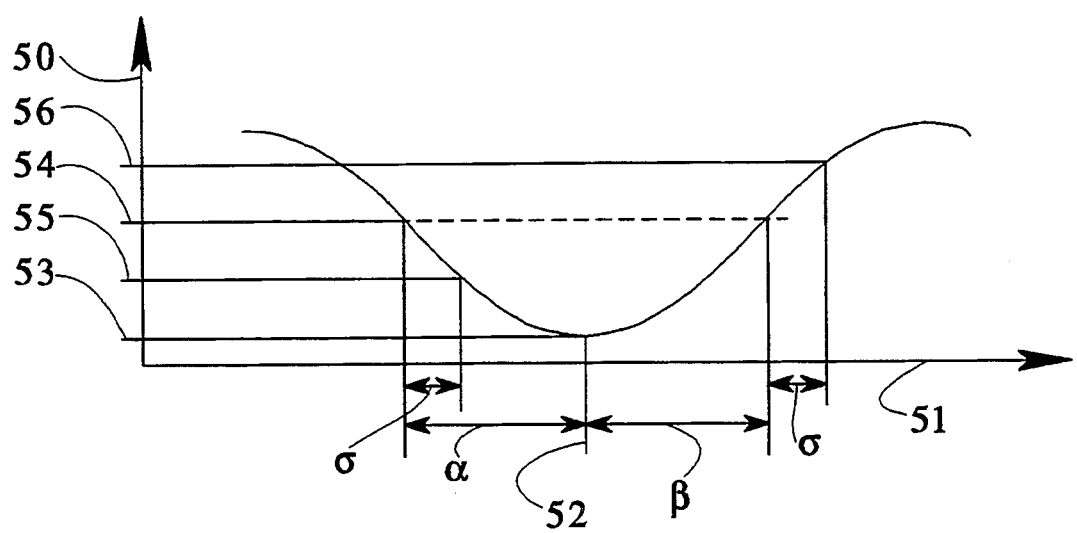
FIG. 3 is a graph depicting an exemplary curve of the photocurrent generated by a detector dependent on the polarization directions of incident light.

The various measured signals registered by the detector 34 are described below with reference to FIG. 3. FIG. 3 illustrates the curve of a photocurrent 50 generated by the detector 34. The curve is dependent on the polarization direction, and on a polarization angle 51 of incident light therewith established for an extremely small depolarization.

A zero angle 52 is defined by the polarization direction for which a linearly polarized light beam incident on the detector 34 generates a minimum photocurrent 53 in the detector 34. The size of the minimum photocurrent 53 is a measure of the depolarization of the incident, incompletely linearly polarized, light beam. With an analyzer having the configuration of analyzer 33, arranged essentially at a right angle relative to the arrow 42, the minimum photocurrent 53 is generated by incident light that is polarized in the direction of the arrow 42.

The first convergent light beam 9 from FIG. 2 has a polarization whose directional angle is smaller than the directional angle of the arrow 42 when angles are measured in a clockwise direction with respect to the arrow 42. The second convergent light beam 29 has a polarization whose directional angle, accordingly, is larger by the angle $\beta$. The angles $\alpha$ and $\beta$ are within a few degrees of one another.

With an optically non-rotating dialysate 11 in the cell 10, and with angles having the same magnitude $|\alpha|=|\beta|$, adjustment photocurrents 54 generated in the detector 34 are then the same. A difference signal between the adjustment photocurrents 54 is zero, and a quotient signal is equal to one.

For detecting the adjustment photocurrents 54, the control and evaluation circuit 37 alternately supplies the light-emitting diodes 1, 21 with current by means of the control lines 38, so that the light-emitting diodes 1, 21 alternately emit light with a switching frequency from a range of, for example, 10 to 1000 Hz inclusive. The emission of the light is preferably also overlaid with a second modulation that is carried out with a frequency from a range of, for example, 1 to 100 kHz inclusive.

Due to the alternating emission of the two light-emitting diodes 1, 21, the two directional angles $\alpha$ and $\beta$ are successively measured, these producing the same adjustment photocurrent 54 given a cell 10 filled with non-rotating dialysate 11. The signal measured in a half-cycle of the switching frequency is intermediately stored in the control and evaluation circuit 37 and is compared, for example in a comparator, to the signal measured in the second half-cycle. In order to enhance the signal-to-noise ratio, the light emission of the two light-emitting diodes 1, 21 is respectively overlaid with the second modulation that enables a phase-sensitive detection of the measured signals with the lock-in amplifier 36.

An optically rotating dialysate 11 further rotates the linear polarization of the convergent light beams 9, 29 passing respectively through the cell 10 by the angle a in the same direction. The light emission of the first light-emitting diode 1 then generates a first signal photocurrent 55 that is allocated to the polarization angle $\alpha+\sigma$. The light emission of the second light-emitting diode 21 generates a second signal photocurrent 56 that is allocated to the polarization angle $\beta+\sigma$. The aggregate angle $\alpha+\sigma$ lies closer to the zero angle 52 than does the aggregate angle $\alpha+\beta$. The first signal photocurrent 55 of the aggregate angle $\alpha+\sigma 0$ is smaller in magnitude than the adjustment photocurrent 54. The second signal photocurrent 56 of the aggregate angle $\alpha+\beta$ is larger in magnitude than the adjustment photocurrent 54.

The first signal photocurrent 55 and the second signal photocurrent 56, generated in the first or second half-cycle of the switching frequency of the light emission of the light-emitting diodes 1, 21, respectively, are unequal in magnitude. The content of optically rotating substances in the dialysate can be calculated by, for example, generating the difference signal proceeding from the intermediately stored, first signal photocurrent 55 and the second signal photocurrent 56, that is unequal to zero, and generating a quotient signal that deviates from the value of one. Any additional comparison signal that is formed from the intermediately stored, first signal photocurrent 55 and from the second signal photocurrent 56 can be utilized for determining the concentration of optically active substances in the dialysate 11.

Figure 4:
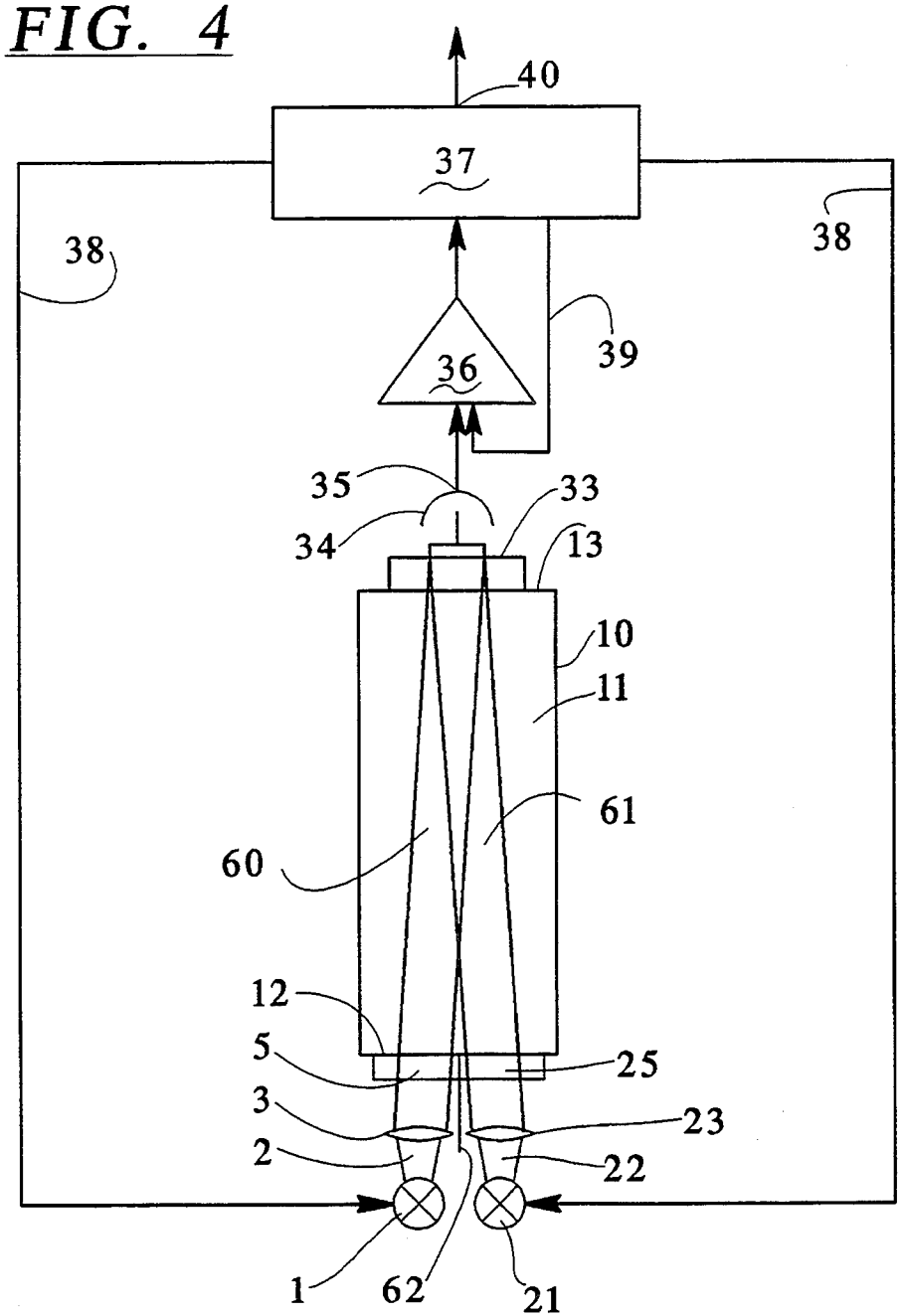
FIG. 4 is a schematic illustration of an apparatus for the quantitative determination of optically active substances conforming to a second exemplary embodiment.

FIG. 4 is a schematic illustration of an apparatus for the quantitative determination of optically active substances in accordance with a second exemplary embodiment. The apparatus includes a first light-emitting diode 1 and a second light-emitting diode 21 that are selected as in the first exemplary embodiment.

It is also assumed for illustration in FIG. 4 that both light-emitting diodes 1, 21 are simultaneously operated. When employing the described apparatus, this only occurs for adjustment or testing purposes; during measuring operation, the two light-emitting diodes 1, 21 emit light intermittently.

The first light-emitting diode 1 generates a first divergent light beam 2. The first divergent light beam 2 is collimated by a first collimator lens 3 and passes through a first polarization filter 5, that linearly polarizes the light emitted by the first light-emitting diode 1. If laser diodes are used, the laser light of the laser diode that replaces the first light-emitting diode 1 is re-polarized by the first polarization filter 5. The polarization of a first imaging light beam 60 that has passed through the first polarization filter 5 should have a polarization ratio of optimally 100:1.

The first imaging light beam 60 passes through the cell 10 that is filled with the dialysate 11 to be analyzed.

The design of the cell 10 can be derived from the first exemplary embodiment.

The second light-emitting diode 21 generates a second divergent light beam 22. The second divergent light beam 22 is collimated by the second collimator lens 23 and passes through the second polarization filter 25, that linearly polarizes the light emitted by the second light-emitting diode 21. If laser diodes are used, the laser light of the laser diode that replaces the second light-emitting diode 21 is re-polarized by the second polarization filter 25. The polarization of a second imaging light beam 61 that is passed through the second polarization filter 25 should have a polarization ratio that corresponds to that of the first imaging light beam 60.

The exact polarization of the second imaging light beam 61 in relationship to the polarization direction of the first imaging light beam 60 is set forth below in conjunction with the illustration of FIG. 2, wherein the light beams provided with reference numerals 9, 29 in FIG. 2 correspond to the light beams 60, 61 for purposes of the discussion below.

The second imaging light beam 61 passes through the cell 10 that is filled with the dialysate 11 to be analyzed.

The two light-emitting diodes 1, 21 and the light beams emanating from them are directed onto the front wall 12 of the cell 10 essentially parallel to the normal of the surface of the cell.

The first polarization filter 5 and the second polarization filter 25 are arranged such that no light of the first light-emitting diode I can be incident onto the second polarization filter 25 and no light of the second light-emitting diode 21 can be incident onto the first polarization filter 5. This can be achieved by an optional partition 62. The two collimator lenses 3, 23 can be replaced by a single collimator lens that combines the imaging properties of the individual lenses.

The two imaging light beams 60, 61 are incident through the transparent back wall 13 of the cell 10 onto the analyzer 33, and are ultimately imaged on the detector 34.

The photosignal 35 of the detector 34, analogous to the first exemplary embodiment, is processed in the lock-in amplifier 36 and in the control and evaluation circuit 37. The drive of the two light-emitting diodes 1, 21 by means of the control lines 38 also ensues in the same way as in the first exemplary embodiment.

In a preferred embodiment, the cell 10 has a cross-sectional area (shown enlarged in FIG. 2) whose side lengths amount to 3 millimeters or, respectively, 6 millimeters. The diameter of the two convergent light beams 9, 29 or, respectively, of the two imaging light beams 60, 61 proceeding in the cell, amounts to approximately 2 millimeters. The length of the cell 10 amounts to a few centimeters. The transparent part of the front wall 12 of the cell can be provides a neutral glass window, or as two polarization filters. 5 and 25. The transparent part of the back wall 13 of the cell is preferably constructed of the analyzer 33. The collimator lenses 3, 23 are connected and glued to the light-emitting diodes 1, 21, and the polarization filters 5, 25 are connected and glued to immersion layers, so that the reflection losses in the beam path are kept low, and the overall optical structure is small and can be mechanically maintained.

A measuring instrument for determining the concentration of optically rotating substances, particularly the chronological variation of the concentration of such substances, that is well suited for implantation in vivo has, for example, a mini battery for energy supply that drives the optical structure of the second exemplary embodiment. Such a structure is constructed without requiring large interspaces between the light sources, and provides for optical alignment with the cell 10 and the measuring and control electronics, in integrated form, and is arranged as an extension of the cell 10.

The control and evaluation circuit 37 can control an insulin pump. The regulating signal 40 of the control and evaluation circuit 37 can be a zero/one signal that places the insulin pump in motion or stops it. It can also be a continuous signal that serves, for example, to display the concentration of an optically rotating substance, or to control a continuously operating pump.

The concentration variation of other optically active substances, that may vary more slowly than that of the sought substance, can be filtered out with corresponding timer elements. For enhancing dynamic range, additional light-emitting diodes can be provided in respective pairs with light having a somewhat different polarization direction in the cross section of the cell 10 through a polarization filter. The second exemplary embodiment illustrates a simple way of configuring such an arrangement. Three or more photocurrents 50 for the various polarization angles 51 in FIG. 3 can be acquired with a square-wave modulation of the light-emission of the light-emitting diodes in three or more clocks having the same length, insofar as possible. The dynamic range of the concentration measurement is considerably increased by a paired selection of suitable signals.

In the first or second exemplary embodiment set forth, the angles $\alpha$ and $\beta$ can also amount to $|\alpha|=|\beta|=45°$. The analyzer 33 can then be arranged both in the described way at a right angle relative to the direction of the arrow 42, illustrated in FIG. 2 as well as in the direction of the arrow 42. This configuration permits the balancing of the light sources in the absence of optically active substances in the measuring path, insofar as the optical light paths do not differ from one another with respect to their transmission or the emitted intensities of the light sources.

Figures 5A, 5B:
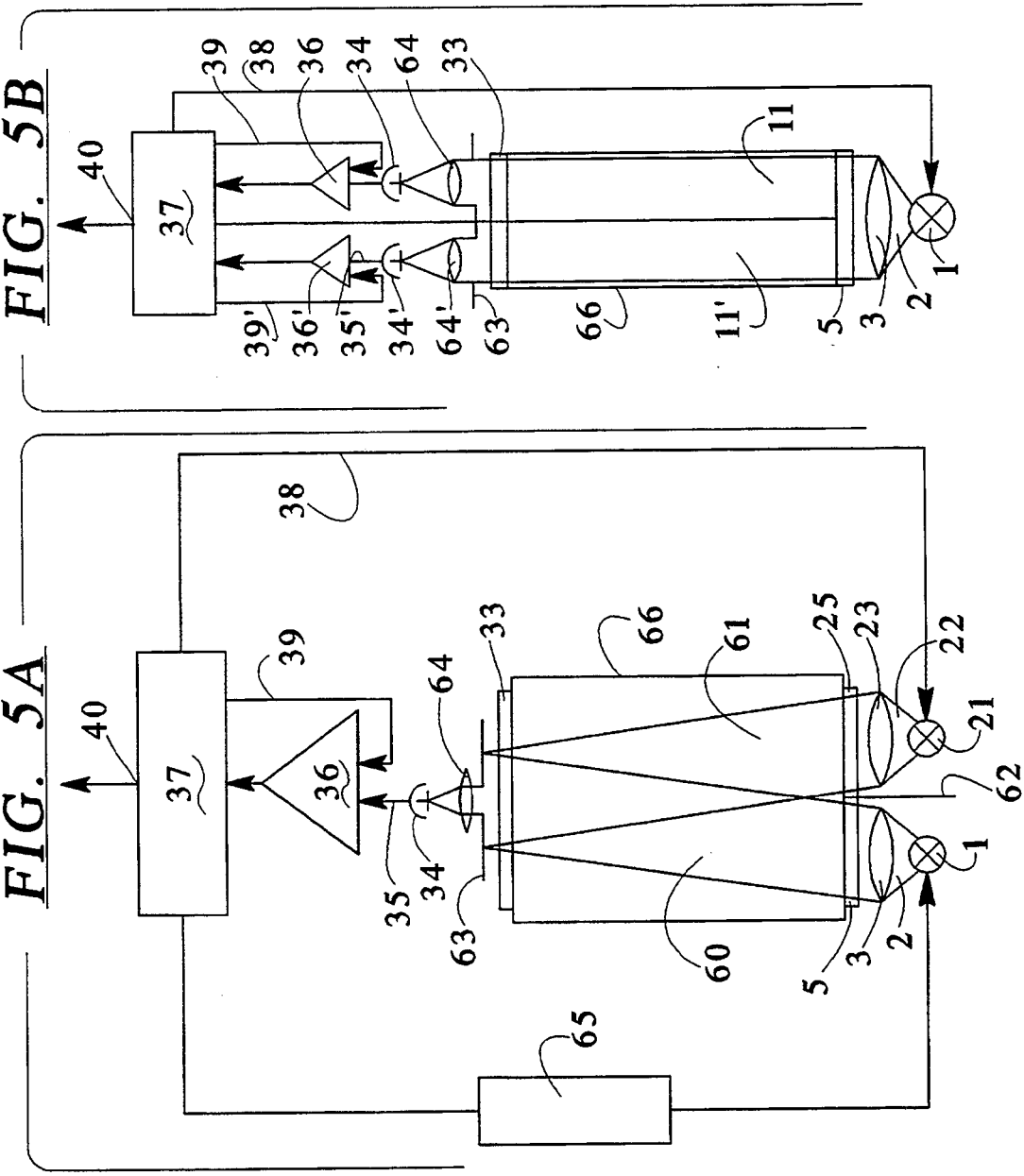
FIGS. 5a and 5b provide a schematic plan view and a schematic side view, respectively, of an apparatus for the quantitative determination of optically active substances conforming to a third exemplary embodiment.

FIGS. 5a and 5b schematically illustrate an apparatus for the quantitative determination of optically active substances in vivo conforming to a third exemplary embodiment of the invention. Compared to the second exemplary embodiment, the third exemplary embodiment has been expanded by a reference beam, and by a reference detector 34'.

FIG. 5b shows a side view of a two-chamber cell 66 whose two chambers respectively contain the measuring fluid or dialysate 11 and a reference fluid 11'. The first light-emitting diode 1 or, respectively, the second light-emitting diode 21 shown in FIG. 5a produce the first divergent light beam 2 and the second divergent light beam 22 that are focused by the first collimator lens 3 or by the second collimator lens 23 to form the first imaging light beam 60 and the second imaging light beam 61. The light beams 60, 61 transilluminate the two chambers of the two-chamber cell 66, as is clearly shown in the side view illustrated in FIG. 5b.

A portion of the light that respectively transilluminates the dialysate 11 and the reference fluid 11' in parallel is gated out with the assistance of an apertured diaphragm 63. The remaining portions of the light beams 60 and 61 that have passed through the dialysate 11 are imaged onto the detector 34 with the assistance of a positive lens 64. The remaining part of the light beams 60 and 61 that have passed through the reference fluid 11' is steered onto the reference detector 34' with the assistance of a second positive lens 64'.

The detector 34 generates the photosignal 35 that charges the lock-in amplifier 36. The output of the lock-in amplifier 36 is connected to an input of the control and evaluation circuit 37. The control and evaluation circuit 37 drives the two light-emitting diodes 1, 21 via control lines 38, and provides a reference signal for the lock-in amplifier 36 via the reference control line 39.

The reference detector 34' generates a reference photosignal 35' that charges a reference lock-in amplifier 36' with the output of the reference lock-in amplifier 36' being connected to a further input of the control and evaluation circuit 37. The control and evaluation circuit 37 provides a reference signal for the reference lock-in amplifier 36' via a second reference control line 39'.

The regulating signal 40 generated in the control and evaluation circuit 37 is employed in a manner analogous to that described with reference to the first exemplary embodiments.

In the absence of optically rotating substances in the reference channel, i.e. in the reference fluid 11', the intensity of the light-emitting diode 1 serving as a radiation source can be balanced by means of an automatically controllable supply circuit 65, such that the reference photosignal 35' of the reference detector 34' is the same for both light-emitting diodes 1, 21, that serve as separate light sources. Such an automatic balancing is of particular advantage given long-term use of the polarimeter, considering the potentially adverse effects of aging on the radiation sources.

The light-emitting diodes 1, 21 emit intermittently with frequencies in the range from below 10 Hz up to a few kHz. The lock-in signal arising within this frequency range allows for signal balancing in the supply circuit 65, in the reference channel, on the basis of zero setting.

The emission of the light is preferably overlaid with a second modulation that is implemented with a frequency ranging from 1 kHz to 100 kHz. The second frequency should be at least one decimal order of magnitude higher than the afore-mentioned, first modulation frequency. The modulation may be achieved by rapid on/off switching of the independently operated light-emitting diode 1, 21. The light-emitting diodes 1, 21 then generate a separate signal for every light source via the reference lock-in amplifier 36', and the resulting signals are matched with the assistance of the automatically controllable supply circuit 65.

Figure 6:
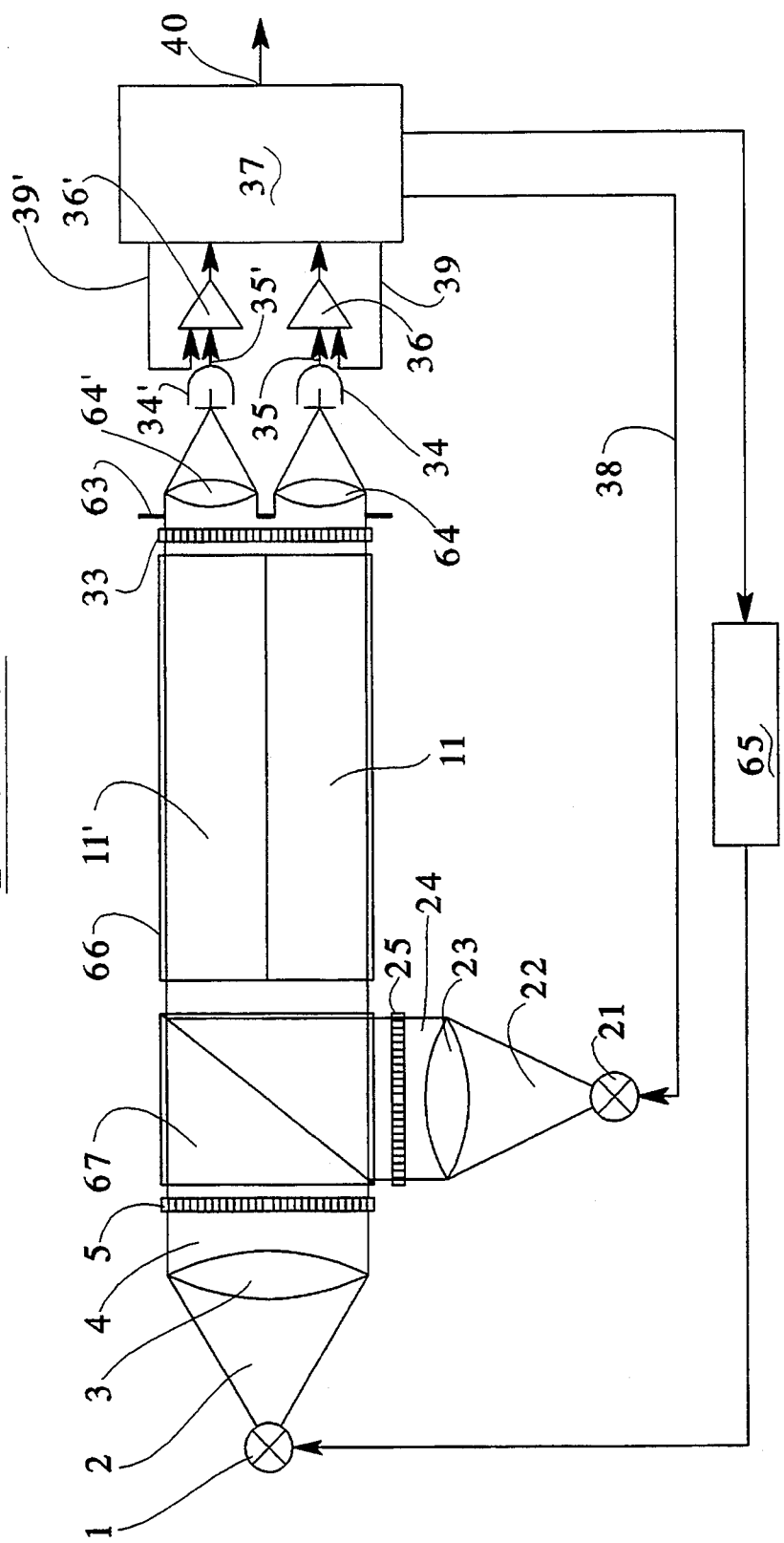
FIG. 6 is a schematic side view of an apparatus for the quantitative determination of optically active substances conforming to a fourth exemplary embodiment.

FIG. 6 schematically illustrates a side view of an apparatus for the quantitative determination of optically active substances in vivo conforming to a fourth exemplary embodiment of the invention. The first divergent light beam 2 emanating from the first light-emitting diode 1 is focused by the first collimator lens 3 to form the first parallel light beam 4 that enters into the two-chamber cell 66 as the first imaging light beam 60 through the first polarization filter 5 and a polarization beam splitter cube 67. The second divergent light beam 22 emanating from the second light-emitting diode 21 is focused by the second collimator lens 23 to form the second parallel light beam 24 that passes through the second polarization filter 25 and, with the polarization beam splitter cube 67, is steered into the two-chamber cell 66, as the second imaging light beam 61.

Both light beams 60, 61 align with one another and preferably have the same beam constriction. When lesser degrees of polarization of the light beams 60 and 61 are needed, the polarization beam splitter cube 67 can be used alone, and the polarization filters 5, 25 can be omitted. It is also possible to utilize a simple, standard, non-depolarizing beam splitter when the polarization filters 5, 25 are employed. The angle between the polarization directions of the two light beams 60, 61 is selected as in preceding exemplary embodiments, particularly at 45° each.

The two-chamber cell 66 contains two chambers that are filled with the dialysate 11 and with the reference fluid 11'. The further beam path and the evaluation of the photosignals 35, 35' thus obtained are analogous to the beam path and photosignal evaluation described with reference to the third exemplary embodiment. The fourth exemplary embodiment has the advantage that the measurement and reference beam paths are identical, so that intensity-attenuating deposits in the measuring beam path do not alter the measured results.

Although other modifications and changes may be suggested by those skilled in the art, it is the intention of the inventors to embody within the patent warranted hereon all changes and modifications as reasonably and properly come within the scope of their contribution to the art.

We claim:

1. A method for the quantitative determination of optically active substances in vivo comprising the steps of:
   (a) generating a first linearly polarized light beam in a first fixed polarization direction with a first light source;
   (b) generating a second linearly polarized light beam in a second fixed polarization direction with a second light source, said second fixed polarization direction deviating by a predetermined angle from said first fixed polarization direction;
   (c) alternatingly transluminating a substance to be analyzed with said first and second linearly polarized light beams, by alternatingly switching said first and second light sources on and off with a switching frequency, to produce first and second substantially alternating beams;
   (d) directing said first and second substantially alternating beams through an analyzer to a detector to produce first and second detector signals, modulating said first and second light sources with a modulation frequency of at least one decimal order of magnitude greater than said switching frequency to phase-sensitively detect said first and second detector signals; and
   (e) generating a comparison signal with said first and second detector signals representative of the concentration of optically active substances in said substance to be analyzed.

2. The method of claim 1, including the step of aligning a polarization direction of said analyzer substantially perpendicular to said first and second fixed polarization directions.

3. The method of claim 11, wherein said predetermined angle is substantially a right angle.

4. The method of claim 3, including the step of aligning a polarization direction of said analyzer substantially 45° from said first fixed polarization direction.

5. The method of claim 3, including the step of aligning a polarization direction of said analyzer substantially 45° from said second fixed polarization direction.

6. An apparatus for the quantitative determination of optically active substance comprising:
   (a) first light source means for selectively generating a first polarized light beam, linearly polarized in a first polarization direction and including a first polarization filter;
   (b) second light source means for selectively generating a second polarized light beam, linearly polarized in a second polarization direction and including a second polarization filter;
   (c) switching means for alternately actuating said first and second light source means;
   (d) analyzer means for collecting said first and second polarized light beams, after passage of said first and second polarized light beams through a substance to be analyzed, and for imaging said first and second polarized light beams;
   (e) detector means for collecting said first and second polarized light beams imaged by said analyzer means and for generating first and second photo signal outputs from said first and second polarized light beams imaged by said analyzer onto said detector means;
   (f) control and evaluation electronic means for selectively storing said first and second photo signal outputs and for generating comparison signals using said first and second photo signal outputs, said comparison signals indicating the concentration of the optically active substance in said substance to be analyzed;
   (g) cell means having a transparent front wall and a transparent back wall and comprising a two chamber cell having a measuring fluid chamber for accepting said substance to be analyzed and a reference fluid chamber;
   (h) a beam splitter cube arranged along a longitudinal axis of said cell means; and
   (i) first and second collimator lenses arranged in conjunction with said first and second light source means respectively, said first collimator lens and said first light source means being arranged along an extension of said longitudinal axis of said cell means, and said second light source means and said second collimator lens being arranged at a substantially right angle relative to said beam splitter cube, said first and second light beams alternately passing through said beam splitter cube, said beam splitter cube alternately splitting said first and second light beams into first and second divergent light beams, said first and second divergent light beams passing through said first and second collimator lenses respectively to form first and second imaging light beams, said first and second imaging light beams further transilluminating said two chamber cell.

7. The apparatus of claim 6, said first and second light source means further comprising first and second light-emitting diodes and first and second polarization filters.

8. The apparatus of claim 6, said first and second light source means further comprising first and second semiconductor laser diodes.

9. The apparatus of claim 8, said first and second light source means further comprising first and second polarization filters.

10. The apparatus of claim 6, wherein said first and second light beams are longitudinally aligned with said cell means.

11. The apparatus of claim 6, wherein said beam splitter cube is a polarization beam splitter cube.

12. The apparatus of claim 6, further comprising a reference detector, said analyzer means collecting said first and second imaging light beams that transilluminate said reference fluid chamber of said two chamber cell and imaging said first and second imaging light beams onto said reference detector.

13. The apparatus of claim 12, said reference detector further comprising a photosignal output connected to said control and evaluation electronics 14. The apparatus of claim 6, wherein said cell means for accepting said substance to be analyzed has a transparent front wall forming said first and second polarization filters and a transparent back wall forming said analyzer means.

* * * * *